(12) United States Patent
Lee et al.

(10) Patent No.: US 10,300,098 B2
(45) Date of Patent: May 28, 2019

(54) CHINESE MEDICINE COMPOSITION FOR TREATING LEUKEMIA BONE MARROW TRANSPLANT FAILURE COMPLICATED BY BRAIN STEM STROKE AFTER CHEMOTHERAPY

(71) Applicant: Chen-Yu Lee, Taipei (TW)

(72) Inventors: Chen-Yu Lee, Taipei (TW); Yuan-Hao Chen, Taipei (TW); Dueng-Yuan Hueng, Taipei (TW)

(73) Assignee: Chen-Yu Lee, Taipei (TW)

( * ) Notice: Subject to any disclaimer, the term of this patent is extended or adjusted under 35 U.S.C. 154(b) by 163 days.

(21) Appl. No.: 15/679,222

(22) Filed: Aug. 17, 2017

(65) Prior Publication Data

US 2019/0054132 A1    Feb. 21, 2019

(51) Int. Cl.

| | | |
|---|---|---|
| *A61K 36/00* | (2006.01) | |
| *A61K 36/40* | (2006.01) | |
| *A61K 36/64* | (2006.01) | |
| *A61K 36/54* | (2006.01) | |
| *A61K 36/8945* | (2006.01) | |
| *A61K 36/284* | (2006.01) | |
| *A61K 36/46* | (2006.01) | |
| *A61K 36/39* | (2006.01) | |
| *A61K 36/076* | (2006.01) | |
| *A61K 36/232* | (2006.01) | |

(52) U.S. Cl.
CPC .......... *A61K 36/40* (2013.01); *A61K 36/076* (2013.01); *A61K 36/232* (2013.01); *A61K 36/284* (2013.01); *A61K 36/39* (2013.01); *A61K 36/46* (2013.01); *A61K 36/54* (2013.01); *A61K 36/64* (2013.01); *A61K 36/8945* (2013.01)

(58) Field of Classification Search
CPC ..................................................... A61K 36/00
See application file for complete search history.

(56) References Cited

U.S. PATENT DOCUMENTS

2004/0185121 A1* 9/2004 Yu .......................... A61K 36/00
424/725

OTHER PUBLICATIONS

Chen-Yu Lee et al., "Acute Lymphocytic Leukemia Bone MarrowTransplant Failure Complicated by Brain Stem Stroke:Complete Recovery Following One Year of Integrated Traditional Chinese Medicine (TCM) and Western Medicine Treatment10-year Follow-up Case Report", The Journal of Chinese-Western Neurology Medicine, Dec. 2016, pp. 100-101.

* cited by examiner

*Primary Examiner* — Qiuwen Mi
(74) *Attorney, Agent, or Firm* — Bacon & Thomas, PLLC

(57) ABSTRACT

A Chinese medicine composition for treating leukemia bone marrow transplant failure complicated by brain stem stroke after chemotherapy, wherein the composition is prepared by the following steps: (A) providing a mixture; (B) mixing the mixture with water and heating the mixture to obtain a crude extract; and (C) filtering the crude extract to remove a residue and obtain a liquid extract; wherein the mixture comprises *Fructus corni, Rehmannia glutinosa, Rhizoma dioscoreae, Angelica sinensis, Cortex eucommiae, Semen cuscutae, Fructus lycii, Cinnamomum cassia, Radix aconiti lateralis preparata, Rhizoma zingiberis, Poria, Cortex phellodendri, Radix achyranthis bidentatae*, and *Atractylodes lancea*.

18 Claims, No Drawings

CHINESE MEDICINE COMPOSITION FOR TREATING LEUKEMIA BONE MARROW TRANSPLANT FAILURE COMPLICATED BY BRAIN STEM STROKE AFTER CHEMOTHERAPY

BACKGROUND OF THE INVENTION

1. Field of the Invention

The present disclosure relates to a composition for treating leukemia bone marrow transplant failure complicated by cerebral vascular disease after chemotherapy, particularly a composition for treating leukemia bone marrow transplant failure complicated by brain stem stroke after chemotherapy.

2. Description of Related Art

As the potential of Chinese medicine for treating disease, Chinese medicine has drawn public's attention in recent years. The principle of herbal medicine application is based on the practice of traditional Chinese medicine theory.

Normal hematopoietic stem cells in the bone marrow constantly proliferate and produce a variety of normal haemocytes. However, patients with leukemia overproduce abnormal leukocytes and produce immature promyelocyte or blast cell, which inhibit hematopoietic function of bone marrow causing bone marrow to reduce the production of normal haemocytes and dramatic decrease in normal erythrocyte, hemoglobin and thrombocyte.

Leukemia can be roughly divided into acute leukemia and chronic leukemia. In comparison with patients with acute leukemia, leukocytes and immature promyelocyte or blast cell are less present in the patients with chronic leukemia, therefore symptoms, such as fever, bleeding, bacterial infection and the like, are less shown in the patients with chronic leukemia. As a result, it is more difficult to treat acute leukemia.

Common treatments of leukemia include chemotherapy, hematopoietic stem cell transplant and the like; chemotherapy is obviously effective but accompanied by serious side effects, patients often cannot get through the treatment regime; and hematopoietic stem cell transplant has numerous defects, which are difficult to match a bone marrow graft, high cost, and the transplant itself causing many complications, therefore, hematopoietic stem cell transplant is usually administered to the patients who do not respond to chemotherapy, the patients who are with leukemia relapse or the patients who belong to high risk group.

The success rate of hematopoietic stem cell transplant, which is commonly known as bone marrow transplant, is about 33%. However, leukemia relapses in many patients receiving hematopoietic stem cell transplant within six months after the surgery; and there is no other effective treatment for the patient with leukemia bone marrow transplant failure, an increase dose of chemotherapy is administered to the patient after the failure, and the patient cannot be cured. Therefore, it is desirable to provide a new therapeutic drug for relieving or curing patients with leukemia bone marrow transplant failure.

SUMMARY OF THE INVENTION

The present disclosure provides a Chinese medicine composition for treating leukemia bone marrow transplant failure complicated by brain stem stroke after chemotherapy, and such Chinese medicine composition can relieve or cure leukemia and improve hemiplegia caused by brain stem stroke. The hematopoietic function in the patient with leukemia bone marrow transplant failure complicated by brain stem stroke is recovered after the treatment, and the patient does not need frequent blood transfusions; furthermore, the patient is able to walk and speak.

The present disclosure provides a Chinese medicine composition for treating leukemia bone marrow transplant failure complicated by brain stem stroke after chemotherapy, wherein the Chinese medicine composition is prepared by the following steps: (A) providing a mixture; (B) mixing the mixture with water and heating the mixture to obtain a crude extract; and (C) filtering the crude extract to remove a residue and obtain a liquid extract; wherein the mixture comprises *Fructus corni, Rehmannia glutinosa, Rhizoma dioscoreae, Angelica sinensis, Cortex eucommiae, Semen cuscutae, Fructus lycii, Cinnamomum cassia, Radix aconiti lateralis preparata, Rhizoma zingiberis, Poria, Cortex phellodendri, Radix achyranthis bidentatae*, and *Atractylodes lancea*.

The mixture of the Chinese medicine composition for treating leukemia bone marrow transplant failure complicated by brain stem stroke after chemotherapy of the present disclosure may further comprise *Herba artemisiae annuae, Rhizoma anemarrhenae*, and *Cortex lycii*.

The preparation steps of the Chinese medicine composition for treating leukemia bone marrow transplant failure complicated by brain stem stroke after chemotherapy of the present disclosure may further comprise: (D) adding a powder of *Ginseng, Cornu cervi pantotrichum, Atractylodes lancea*, or a combination thereof to the liquid extract.

The amount of water used in the present disclosure preferably is 450-650 parts by weight, more preferably 500-600 parts by weight; wherein the part by weight of the water is 3.75 grams per part.

In one embodiment of the present disclosure, preferably, the mixture comprises 2-6 parts by weight of *Fructus corni*, 2-6 parts by weight of *Rehmannia glutinosa*, 2-6 parts by weight of *Rhizoma dioscoreae*, 0.5-4 parts by weight of *Angelica sinensis*, 2-6 parts by weight of *Cortex eucommiae*, 2-6 parts by weight of *Semen cuscutae*, 1-5 parts by weight of *Fructus lycii*, 3-7 parts by weight of *Cinnamomum cassia*, 1-5 parts by weight of *Radix aconiti lateralis preparata*, 1-5 parts by weight of *Rhizoma zingiberis*, 1-5 parts by weight of *Poria*, 1-5 parts by weight of *Cortex phellodendri*, 3-7 parts by weight of *Radix achyranthis bidentatae*, and 1-5 parts by weight of *Atractylodes lancea*; more preferably, 3-5 parts by weight of *Fructus corni*, 3-5 parts by weight of *Rehmannia glutinosa*, 3-5 parts by weight of *Rhizoma dioscoreae*, 1-3 parts by weight of *Angelica sinensis*, 3-5 parts by weight of *Cortex eucommiae*, 3-5 parts by weight of *Semen cuscutae*, 2-4 parts by weight of *Fructus lycii*, 4-6 parts by weight of *Cinnamomum cassia*, 2-4 parts by weight of *Radix aconiti lateralis preparata*, 2-4 parts by weight of *Rhizoma zingiberis*, 2-4 parts by weight of *Poria*, 2-4 parts by weight of *Cortex phellodendri*, 4-6 parts by weight of *Radix achyranthis bidentatae*, and 2-4 parts by weight of *Atractylodes lancea*. The part by weight of the mixture is 3.75 grams per part.

In another embodiment of the present disclosure, preferably, the mixture comprises 2-6 parts by weight of *Fructus corni*, 2-6 parts by weight of *Rehmannia glutinosa*, 2-6 parts by weight of *Rhizoma dioscoreae*, 0.5-4 parts by weight of *Angelica sinensis*, 2-6 parts by weight of *Cortex eucommiae*, 2-6 parts by weight of *Semen cuscutae*, 1-5 parts by weight of *Fructus lycii*, 4-12 parts by weight of *Cinnamomum cassia*, 1-5 parts by weight of *Radix aconiti lateralis pre-*

*parata*, 3-9 parts by weight of *Rhizoma zingiberis*, 1-5 parts by weight of *Poria*, 1-5 parts by weight of *Cortex phellodendri*, 3-7 parts by weight of *Radix achyranthis bidentatae*, 1-5 parts by weight of *Atractylodes lancea*, 2-6 parts by weight of *Herba artemisiae annuae*, 2-6 parts by weight of *Rhizoma anemarrhenae*, and 2-6 parts by weight of *Cortex lycii*; more preferably, 3-5 parts by weight of *Fructus corni*, 3-5 parts by weight of *Rehmannia glutinosa*, 3-5 parts by weight of *Rhizoma dioscoreae*, 1-3 parts by weight of *Angelica sinensis*, 3-5 parts by weight of *Cortex eucommiae*, 3-5 parts by weight of *Semen cuscutae*, 2-4 parts by weight of *Fructus lycii*, 6-10 parts by weight of *Cinnamomum cassia*, 2-4 parts by weight of *Radix aconiti lateralis preparata*, 4-7 parts by weight of *Rhizoma zingiberis*, 2-4 parts by weight of *Poria*, 2-4 parts by weight of *Cortex phellodendri*, 4-6 parts by weight of *Radix achyranthis bidentatae*, 2-4 parts by weight of *Atractylodes lancea*, 3-5 parts by weight of *Herba artemisiae annuae*, 3-5 parts by weight of *Rhizoma anemarrhenae*, and 3-5 parts by weight of *Cortex lycii*. Preferably, the part by weight of the mixture is 3.75 grams per part.

In another embodiment of the present disclosure, the powder content of step (D) is not particularly limited. Preferably, the powder comprises powder of 1-5 parts by weight of *Ginseng*, 1-3 parts by weight of *Cornu cervi pantotrichum*, 2-6 parts by weight of *Atractylodes lancea*, or a combination thereof. More preferably, the powder comprises a powder of 2-4 parts by weight of *Ginseng*, 1-3 parts by weight of *Cornu cervi pantotrichum*, 3-5 parts by weight of *Atractylodes lancea*, or a combination thereof. Preferably, the weight per part of the powder is 3.75 grams per part.

The method of decocting herbal medicine used in the present invention is not particularly limited and may be carried out by any method known in the art. The method of "heating" used in the present invention is not particularly limited and may be carried out by any method known in the art such as direct heating, water heating, and the like.

Other objects, advantages, and novel features of the invention will become more apparent from the following detailed description.

DETAILED DESCRIPTION OF THE PREFERRED EMBODIMENT

Unless otherwise specified, all technical and scientific terms set forth in the specification and claims of the present invention are defined as follows. The singular term "a", "an", or "the", unless otherwise specified, refers to more than one object. The term "or" or "and" used herein, unless otherwise specified, refers to "and/or". In addition, the term "include" or "comprise" used herein are open ended conjunctions. The preceding paragraphs are merely systematic references and should not be construed as limiting the subject matter of the invention. Unless otherwise specified, the materials used herein are commercially available, and the ways to get materials listed below are merely exemplary.

Preparation Example 1: Preparation of an Extract-1 of a Mixture

Four parts by weight of *Fructus corni*, 4 parts by weight of *Rehmannia glutinosa*, 4 parts by weight of *Rhizoma dioscoreae*, 2 parts by weight of *Angelica sinensis*, 4 parts by weight of *Cortex eucommiae*, 4 parts by weight of *Semen cuscutae*, 3 parts by weight of *Fructus lycii*, 5 parts by weight of *Cinnamomum cassia*, 3 parts by weight of *Radix aconiti lateralis preparata*, 3 parts by weight of *Rhizoma zingiberis*, 3 parts by weight of *Poria*, 3 parts by weight of *Cortex phellodendri*, 5 parts by weight of *Radix achyranthis bidentatae*, and 3 parts by weight of *Atractylodes lancea* were provided, decocted with 530 parts by weight of water to form a crude extract of 120 parts by weight, and the crude extract was filtered to remove a residue and obtain an extract-1 of the mixture.

Preparation Example 2: Preparation of an Extract-2 of a Mixture

Four parts by weight of *Fructus corni*, 4 parts by weight of *Rehmannia glutinosa*, 4 parts by weight of *Rhizoma dioscoreae*, 2 parts by weight of *Angelica sinensis*, 4 parts by weight of *Cortex eucommiae*, 4 parts by weight of *Semen cuscutae*, 3 parts by weight of *Fructus lycii*, 8 parts by weight of *Cinnamomum cassia*, 3 parts by weight of *Radix aconiti lateralis preparata*, 5 parts by weight of *Rhizoma zingiberis*, 3 parts by weight of *Poria*, 3 parts by weight of *Cortex phellodendri*, 5 parts by weight of *Radix achyranthis bidentatae*, 3 parts by weight of *Atractylodes lancea*, 4 parts by weight of *Herba artemisiae annuae*, 4 parts by weight of *Rhizoma anemarrhenae*, and 4 parts by weight of *Cortex lycii* were provided, decocted with 540 parts by weight of water to form a crude extract of 120 parts by weight, and the crude extract was filtered to remove a residue and obtain an extract-2 of a mixture.

Preparation Example 3: Preparation of Composition-1 for Treating Leukemia Bone Marrow Transplant Failure Complicated by Brain Stem Stroke after Chemotherapy As described in the above preparation examples, the extract-1 of the mixture is a composition-1 for treating leukemia bone marrow transplant failure complicated by brain stem stroke after chemotherapy.

Preparation Example 4: Preparation of Composition-2 for Treating Leukemia Bone Marrow Transplant Failure Complicated by Brain Stem Stroke after Chemotherapy As described in the above preparation examples, the extract-2 of the mixture is a composition-2 for treating leukemia bone marrow transplant failure complicated by brain stem stroke after chemotherapy.

Preparation Example 5: Preparation of Composition-3 for Treating Leukemia Bone Marrow Transplant Failure Complicated by Brain Stem Stroke after Chemotherapy The extract-1 was provided, and added with a powder of 3 parts by weight of *Ginseng* and 1 part by weight of *Cornu cervi* to obtain a composition-3 for treating leukemia bone marrow transplant failure complicated by brain stem stroke after chemotherapy.

Preparation Example 6: Preparation of Composition-4 for Treating Leukemia Bone Marrow Transplant Failure Complicated by Brain Stem Stroke after Chemotherapy The extract-1 of the mixture was provided, and added with a powder of 4 parts by weight of *Atractylodes lancea* to obtain a composition-4 for treating leukemia bone marrow transplant failure complicated by brain stem stroke after chemotherapy.

Preparation Example 7: Preparation of Composition-5 for Treating Leukemia Bone Marrow Transplant Failure Complicated by Brain Stem Stroke after Chemotherapy The extract-2 of the mixture was provided, and added with a powder of 3 parts by weight of *Ginseng* and 2 parts by weight *Cornu cervi* to obtain a composition-5 for treating leukemia bone marrow transplant failure complicated by brain stem stroke after chemotherapy.

Embodiment 1

The patient of Embodiment 1 is female and is a patient with acute lymphocytic leukemia. The patient received chemotherapy followed by bone marrow transplant. One year after receiving bone marrow transplant, the bone marrow did not function in the patient, and hemorrhage shown in the right section of the brain about 2 weeks after receiving bone marrow transplant; and the patient had left-sided hemiplegia and needed a ventilator to assist breathing. Abnormal cells were not found in the patient according to the result of bone marrow aspiration; and although the bone marrow graft was found in the patient, it grew slowly. The patient needed a whole blood transfusion once every two weeks and 1-2 unit thrombocyte transfusion once per week; and after the transfusion, the amount of thrombocyte rose to about 100,000 right away but dropped to 10,000 seven days later.

The treatment for the patient of Embodiment 1 comprised: from day 1, composition-1 for treating leukemia bone marrow transplant failure complicated by brain stem stroke after chemotherapy was administered to the patient once per day. Two weeks later, the patient started to speak; one month later, the patient was able to bend left foot and did not need a ventilator during daytime; three months later, the patient was able to speak normally; five months later, the patient did not to have transfusions; and seven months later, the patient was able to walk on her own. The patient's hemoglobin, leukocyte and thrombocyte levels were in the normal ranges according to the follow-up report.

Embodiments 2

The patient of Embodiment 2 is about 40 years old and is a patient with acute lymphocytic leukemia. The patient received chemotherapy followed by bone marrow transplant. The bone marrow did not function in the patient and the complication of hematoma shown in the brain; the patient was unable to speak, had hemiplegia, relied on a ventilator to assist breathing, and needed regular blood transfusions to stay alive.

The treatment for the patient of Embodiment 2 comprised: from day 1, composition-2 for treating leukemia bone marrow transplant failure complicated by brain stem stroke after chemotherapy was administered to the patient once per day. One month later, the patient reduced the frequency of using a ventilator, two months later, the patient was able to wave; three months later, the patient did not need to rely on a ventilator to assist breathing and could breathe on the patient's own; four months later, the patient was able to speak normally; seven months later, the patient did not need blood transfusions; nine months later, the patient started to learn standing and walking on the patient's own; and one year later, the patient got back to work.

Embodiment 3

In the present embodiment, the patient received chemotherapy followed by bone marrow transplant. After receiving bone marrow transplant, the bone marrow did not function in the patient; 2 weeks later, the patient had cerebral hemorrhage, was unable to speak, was unable to urinate on the patient's own, relied on a ventilator to assist breathing, and needed transfusions to stay alive.

The treatment for the patient of Embodiment 3 comprised: from day 1, composition-1 for treating leukemia bone marrow transplant failure complicated by brain stem stroke after chemotherapy was administered to the patient once per day; one month later, the patient did not need a ventilator during daytime and only used it at night; two months later, the patient was able to wave and bend feet; three months later, the patient was able to speak, the composition-1 was no more administered and composition-3 for treating leukemia bone marrow transplant failure complicated by brain stem stroke after chemotherapy was administered to the patient; five month later, the patient was able to urinate on the patient's own; six months later, the patient did not need transfusions; eight months later, the patient was able to seat and learn standing; and ten months later, the patient was able to tie things with both hands. During the treatment regime, composition-1 may be replaced with composition-4 if there was a need for relieving diarrhea, and the composition-4 was administered to the patient once per day.

Embodiment 4

By bone marrow aspiration, it was found that myeloid-to-erythroid ratio (M/E) is 5:1 in the patient of Embodiment 4, wherein the normal M/E is 2:1; and M/E increase referred to acute or chronic infection, leukaemoid reaction, or acute or chronic myeloid leukemia. The patient received chemotherapy followed by bone marrow transplant. One year after receiving bone marrow transplant, the bone marrow did not function in the patient, brain stem stroke and left-sided hemiplegia shown in the patient; the patient was unable to speak and needed a ventilator to assist breathing, and needed whole blood transfusion once every two weeks, and 1-2 unit thrombocyte transfusion once per week to stay alive.

The treatment for the patient of Embodiment 4 comprised: from day 1, composition-5 for treating leukemia bone marrow transplant failure complicated by brain stem stroke after chemotherapy was administered to the patient once per day. One month later, the patient did not need to a ventilator during daytime and the patient's left hand became more agile; three months later, the patient was able to speak clearly and did not need a ventilator; five months later, the patient did not need a thrombocyte transfusion; seven months later, the patient did not need transfusions; nine months later, the patient was able to walk; and eleven months later, the patient was able to use both hands. The patient's hemoglobin, leukocyte and thrombocyte levels were in the normal ranges according to the follow-up report, which meant the hematopoietic function was normal; and the leukemia did not relapse.

Although the present invention has been explained in relation to its preferred embodiment, it is to be understood that many other possible modifications and variations can be made without departing from the spirit and scope of the invention as hereinafter claimed.

What is claimed is:

1. A Chinese medicine composition for treating leukemia bone marrow transplant failure complicated by brain stem stroke after chemotherapy, wherein the Chinese medicine composition is prepared by the following steps:
(A) providing a mixture;
(B) mixing the mixture with water and heating the mixture to obtain a crude extract; and
(C) filtering the crude extract to remove a residue and obtain a liquid extract;
wherein the mixture comprises *Fructus corni, Rehmannia glutinosa, Rhizoma dioscoreae, Angelica sinensis, Cortex eucommiae, Semen cuscutae, Fructus lycii, Cinnamomum cassia, Radix aconiti lateralis preparata, Rhizoma zingiberis, Poria, Cortex phellodendri, Radix achyranthis bidentatae*, and *Atractylodes lancea*.

2. The Chinese medicine composition as claimed in claim 1, wherein the amount of the water is 500-600 parts by weight.

3. The Chinese medicine composition as claimed in claim 2, wherein the part by weight of the water is 3.75 grams per part.

4. The Chinese medicine composition as claimed in claim 1, wherein the mixture comprises 2-6 parts by weight of *Fructus corni*, 2-6 parts by weight of *Rehmannia glutinosa*, 2-6 parts by weight of *Rhizoma dioscoreae*, 0.5-4 parts by weight of *Angelica sinensis*, 2-6 parts by weight of *Cortex eucommiae*, 2-6 parts by weight of *Semen cuscutae*, 1-5 parts by weight of *Fructus lycii*, 3-7 parts by weight of *Cinnamomum cassia*, 1-5 parts by weight of *Radix aconiti lateralis preparata*, 1-5 parts by weight of *Rhizoma zingiberis*, 1-5 parts by weight of *Poria*, 1-5 parts by weight of *Cortex phellodendri*, 3-7 parts by weight of *Radix achyranthis bidentatae*, and 1-5 parts by weight of *Atractylodes lancea*.

5. The Chinese medicine composition as claimed in claim 4, wherein the part by weight of the mixture is 3.75 grams per part.

6. The Chinese medicine composition as claimed in claim 5, wherein the mixture comprises 3-5 parts by weight of *Fructus corni*, 3-5 parts by weight of *Rehmannia glutinosa*, 3-5 parts by weight of *Rhizoma dioscoreae*, 1-3 parts by weight of *Angelica sinensis*, 3-5 parts by weight of *Cortex eucommiae*, 3-5 parts by weight of *Semen cuscutae*, 2-4 parts by weight of *Fructus lycii*, 4-6 parts by weight of *Cinnamomum cassia*, 2-4 parts by weight of *Radix aconiti lateralis preparata*, 2-4 parts by weight of *Rhizoma zingiberis*, 2-4 parts by weight of *Poria*, 2-4 parts by weight of *Cortex phellodendri*, 4-6 parts by weight of *Radix achyranthis bidentatae*, and 2-4 parts by weight of *Atractylodes lancea*.

7. The Chinese medicine composition as claimed in claim 1, wherein the mixture further comprises *Herba artemisiae annuae, Rhizoma anemarrhenae*, and *Cortex lycii*.

8. The Chinese medicine composition as claimed in claim 7, wherein the mixture comprises 2-6 parts by weight of *Fructus corni*, 2-6 parts by weight of *Rehmannia glutinosa*, 2-6 parts by weight of *Rhizoma dioscoreae*, 0.5-4 parts by weight of *Angelica sinensis*, 2-6 parts by weight of *Cortex eucommiae*, 2-6 parts by weight of *Semen cuscutae*, 1-5 parts by weight of *Fructus lycii*, 4-12 parts by weight of *Cinnamomum cassia*, 1-5 parts by weight of *Radix aconiti lateralis preparata*, 3-9 parts by weight of *Rhizoma zingiberis*, 1-5 parts by weight of *Poria*, 1-5 parts by weight of *Cortex phellodendri*, 3-7 parts by weight of *Radix achyranthis bidentatae*, 1-5 parts by weight of *Atractylodes lancea*, 2-6 parts by weight of *Herba artemisiae annuae*, 2-6 parts by weight of *Rhizoma anemarrhenae*, and 2-6 parts by weight of *Cortex lycii*.

9. The Chinese medicine composition as claimed in claim 8, wherein the part by weight of the composition is 3.75 grams.

10. The Chinese medicine composition as claimed in claim 9, wherein the mixture comprises 3-5 parts by weight of *Fructus corni*, 3-5 parts by weight of *Rehmannia glutinosa*, 3-5 parts by weight of *Rhizoma dioscoreae*, 1-3 parts by weight of *Angelica sinensis*, 3-5 parts by weight of *Cortex eucommiae*, 3-5 parts by weight of *Semen cuscutae*, 2-4 parts by weight of *Fructus lycii*, 6-10 parts by weight of *Cinnamomum cassia*, 2-4 parts by weight of *Radix aconiti lateralis preparata*, 4-7 parts by weight of *Rhizoma zingiberis*, 2-4 parts by weight of *Poria*, 2-4 parts by weight of *Cortex phellodendri*, 4-6 parts by weight of *Radix achyranthis bidentatae*, 2-4 parts by weight of *Atractylodes lancea*, 3-5 parts by weight of *Herba artemisiae annuae*, 3-5 parts by weight of *Rhizoma anemarrhenae*, and 3-5 parts by weight of *Cortex lycii*.

11. The Chinese medicine composition as claimed in claim 1, further comprising step
(D) adding a powder of *Ginseng, Cornu cervi* pantotrichum, *Atractylodes lancea*, or a combination thereof to the liquid extract.

12. The Chinese medicine composition as claimed in claim 11, wherein the step (D) a powder of 1-5 parts by weight of *Ginseng*, 1-3 parts by weight of *Cornu cervi* pantotrichum, 2-6 parts by weight of *Atractylodes lancea*, or a combination thereof is added.

13. The Chinese medicine composition as claimed in claim 12, wherein the part by weight of the powder is 3.75 grams per part.

14. The Chinese medicine composition as claimed in claim 13, wherein the step (D) a powder of 2-4 parts by weight of *Ginseng*, 1-3 parts by weight of *Cornu cervi* pantotrichum, 3-5 parts by weight of *Atractylodes lancea*, or a combination thereof is added.

15. The Chinese medicine composition as claimed in claim 7, further comprising step
(D) adding a powder of *Ginseng, Cornu cervi* pantotrichum, *Atractylodes lancea*, or a combination thereof to the liquid extract.

16. The Chinese medicine composition as claimed in claim 15, wherein the step (D) a powder of 1-5 parts by weight of *Ginseng*, 0.1-3 parts by weight of *Cornu cervi* pantotrichum, 2-6 parts by weight of *Atractylodes lancea*, or a combination thereof is added.

17. The Chinese medicine composition as claimed in claim 16, wherein the part by weight of the powder is 3.75 grams per part.

18. The Chinese medicine composition as claimed in claim 17, wherein the step (D) a powder of 2-4 parts by weight of *Ginseng*, 0.5-2 parts by weight of *Cornu cervi* pantotrichum, 3-5 parts by weight of *Atractylodes lancea*, or a combination thereof is added.

* * * * *